United States Patent [19]

Nichols et al.

[11] Patent Number: 5,028,707
[45] Date of Patent: Jul. 2, 1991

[54] 4-HYDROXYQUINALDIC ACID DERIVATIVES

[75] Inventors: Alfred C. Nichols, Texas City; K. Lemone Yielding, Galveston, both of Tex.

[73] Assignee: Board of Regents, University of Texas, Austin, Tex.

[21] Appl. No.: 439,652

[22] Filed: Nov. 20, 1989

[51] Int. Cl.$^5$ ............... C07D 215/18; C07D 215/233
[52] U.S. Cl. .................................... 546/156; 424/1.1; 514/312; 530/350; 546/153
[58] Field of Search ............................. 546/153, 156

[56] References Cited

U.S. PATENT DOCUMENTS 3,932,416  1/1976  Bays et al. .......................... 546/156
4,299,831  11/1981  Clemence et al. ................. 546/156
4,804,760  2/1989  Schriewer et al. ................. 546/153

OTHER PUBLICATIONS

C.A., vol. 70, No. 15, Abs. No. 67414b, 1969.
C.A., vol. 70, No. 15, Abs. No. 68087j, 1969.
C.A., vol. 70, No. 19, Abs. No. 87512k, 1969.
C.A., vol. 80, No. 25, Abs. No. 14617h, 1974.
C.A., vol. 95, No. 11, Abs. No. 97542a, 1981.
C.A., vol. 97, No. 3, Abs. No. 16653d, 1982.
Barnes *Science* 239:254–256 (1988).
Kochhar et al.; *Arch. Neurol* 45:148–153 (1988).
Wielock et al.; *Science* 230:681–683 (1985).
Snell et al.; *European Journal of Pharmacol.* 156:105–110 (1988).
Kemp et al.; *Proc. Natl. Acad. Sci. U.S.A.* 85:6547–6550 (1988).
Saikachi et al.; *Chem. Pharm. Bull.* 29(1):237–244 (1981).
Hanstein; *Methods in Anzymology*, pp. 653–683.
Cotman et al.; *J. HIN Research* 1:65–74 (1989).
Dialog Search dated Jul. 26, 1989.

*Primary Examiner*—Richard L. Raymond
*Assistant Examiner*—Susan P. Treanor
*Attorney, Agent, or Firm*—Arnold, White, & Durkee

[57] ABSTRACT

A 7-chloro-4-hydroxy-2-quinoline carbonyl azide and its use as a photoaffinity probe for the N-methyl-D-aspartate (NMDA) receptor complex on neurons are claimed. A number of other compounds, including 4-hydroxy-2-quinoline carbonyl azides, isocyanates, and amides are also provided. Purification and characterization of the NMDA receptor is described.

17 Claims, 5 Drawing Sheets

4-HYDROXYQUINALDIC ACID DERIVATIVES

I. FIELD OF THE INVENTION

This invention relates to 4-hydroxyquinaldic acid derivatives, and more specifically to a 7-chloro-4-hydroxy-2quinoline carbonyl azide and its use as a photoaffinity probe for the N-methyl-D-aspartate (NMDA) receptor complex on neurons. The invention also provides a number of other 4-hydroxy-2-quinoline carbonyl azides, isocyanates, and amides. Purification and characterization of the NMDA receptor is also described.

II. BACKGROUND OF THE INVENTION

Neurons of the central nervous system (CNS) possess a number of cell surface receptors, each of which can be activated by a selective amino acid analogue. One of the most important of those receptors is the "NMDA" receptor, which takes its name from N-methyl-D-aspartate, an amino acid that stimulates the receptor. Since NMDA does not occur naturally in the brain, it is believed that amino acid neurotransmitters such as glutamate or aspartate probably stimulate NMDA receptors in vivo.

When glutamate or NMDA binds to the receptor complex, membrane pores (ion channels) open, allowing cations to diffuse through the channels, resulting in excitation of the cell. This process is essential for normal brain functions such as learning and appropriate control of motor activity. Excessive excitation at this receptor has been implicated in the rapid and irreversible damage of brain tissue which follows injury or deprivation of oxygen or energy sources. There is also evidence that the NMDA receptor complex may play a role in degenerative disorders such as Huntington's chorea and Alzheimer's disease, and in the etiology of epilepsy.

Therefore, pharmacologic control of such binding, which can come from an understanding of the specific receptor molecules and the subsequent biological processes involved, is a much sought after goal. Potentially, it should be possible to optimize 'normal' learning, prevent certain degenerative disorders, assist in the rehabilitation of individuals who have been compromised by ischemic injury or degenerative diseases, and prevent or control certain types of epileptic seizures. Unfortunately, the study of the NMDA receptor and other amino acid specific receptors has been difficult because only crude preparations of brain cell membranes could be used as the source of receptors, and the structural basis for receptor activation is not completely understood.

It is known that the NMDA receptor complex in brain tissue has binding sites for drugs, excitatory neurotransmitters, modulating amino acid ligands, and cations. The consequences for nerve function depend on the interactions of the various ligands. The amino acid glycine potentiates NMDA receptor response through a glycine recognition site that is part of the NMDA receptor complex but is separate from the NMDA or glutamate binding site. Recently, Kemp, et al., reported that 7-chlorokynurenic acid is a selective antagonist of the glycine modulatory site. (*Proc. Nat'l. Acad. Sci. USA* 85:6547-6550, 1988). However, the receptor was neither characterized nor preferred by that group.

Glycine also serves as a neurotransmitter in the spinal cord, where it binds to a strychnine sensitive receptor. Although this binding site is functionally different from that found on the NMDA receptor complex, it too is physiologically very important. There is a corresponding need to isolate and study this receptor, which may be involved in spinal cord degeneration and seizures.

Therefore, a great need remains for compounds that can be used for isolation of such receptors and methods and reagents for facilitating receptor isolation.

SUMMARY

Fortunately, the present inventors have now designed a novel photoaffinity labeling reagent capable of covalently coupling a fluorescent molecule to glycine binding sites such as those found on the NMDA receptor. This reagent will specifically label a protein having such a binding site. In a highly preferred embodiment, the invention comprises a compound having the formula:

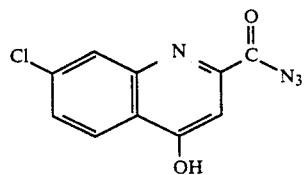

The invention also includes a more generic class of 4-hydroxyquinaldic acid derivatives, which may be represented by the following formula:

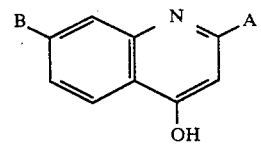

wherein A is selected from azide, amide, or isocyanate; and wherein B is hydrogen or a halogen.

Also included are compounds of the formula:

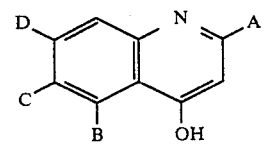

wherein A is azide, amide or isocyanate; wherein B is chloro or hydrogen; wherein C is methoxy or hydrogen; and wherein D is chloro, bromo, iodo, or fluoro.

Preferred species include 7-bromo-4-hydroxy-2-quinoline carbonyl azide, 7-bromo-4-hydroxy-2-quinoline isocyanate, 7-bromo-4-hydroxy-2-quinolamide, 7-fluoro-4-hydroxy-2-quinoline carbonyl azide, 7-iodo-4-hydroxy-2-quinoline carbonyl azide, 7-iodo-4-hydroxy-2-quinoline isocyanate, 7-iodo-4-hydroxy-2-quinolamide, 6-methoxy-4-hydroxy-2-quinoline carbonyl azide, 6-methoxy-4-hydroxy-2-quinolamide, 6-methoxy-4-hydroxy-2-quinoline isocyanate, 7-chloro-6-methoxy-4-hydroxy-2-quinoline carbonyl azide, 7-chloro-6-methoxy-4-hydroxy-2-quinolamide, 7-chloro-6-methoxy-4-hydroxy-2-quinoline isocyanate, 5-chloro-4-hydroxy-2-quinoline carbonyl azide, 5-chloro-4-hydroxy-2-quinoline isocyanate, and 5-chloro-4-hydroxy-2-quinolamide.

The 7-chloro-4-hydroxy-2-quinoline carbonyl azide has been used to label NMDA receptor proteins, facilitating isolation of such proteins in substantially purified form for the first time. Accordingly, the present invention also includes a method for labeling NMDA receptors comprising obtaining a preparation containing said receptors; exposing said preparation to 7-chloro-4-hydroxy-2-quinoline carbonyl azide under such conditions that the compound binds to said receptors; and irradiating said bound composition with light to covalently bond said compound to said receptors to form a fluorescent-receptor complex. In an additional embodiment directed toward substantial purification of the factor, the method comprises the additional step of electrophoresing the fluorescent receptor complex through a gel matrix, such as a polyacrylamide gel. This procedure successfully identified at least two membrane components, one with a relative molecular weight ($M_r$) of between about 25,000 and 30,000, more particularly about 29,000, and another with a realtive molecular weight at about 40,000 to 45,000 $M_r$ and more particularly about 43,000 $M_r$. Accordingly, in a related embodiment, the invention includes a substantially purified cell surface membrane protein having the ability to become fluorescently labeled upon incubation with 7-chloro-4-hydroxy-2quinoline carbonyl azide, followed by irradiation with ultraviolet light; and a molecular weight of about 25,000–30,000 $M_r$, as determined by polyacrylamide gel electrophoresis under reducing conditions. The invention also includes a substantially purified cell surface membrane protein having the ability to become fluorescently labeled upon incubation with 7-chloro-4-hydroxy-2-quinoline carbonyl azide, followed by irradiation with ultraviolet light; and a molecular weight of about 40,000–45,000 $M_r$, as determined by polyacrylamide gel electrophoresis under reducing conditions.

These and other features of the present invention may be more readily understood by referring to the following drawings and description of preferred embodiments

DETAILED DESCRIPTION OF A PREFERRED EMBODIMENT

Figure 1:
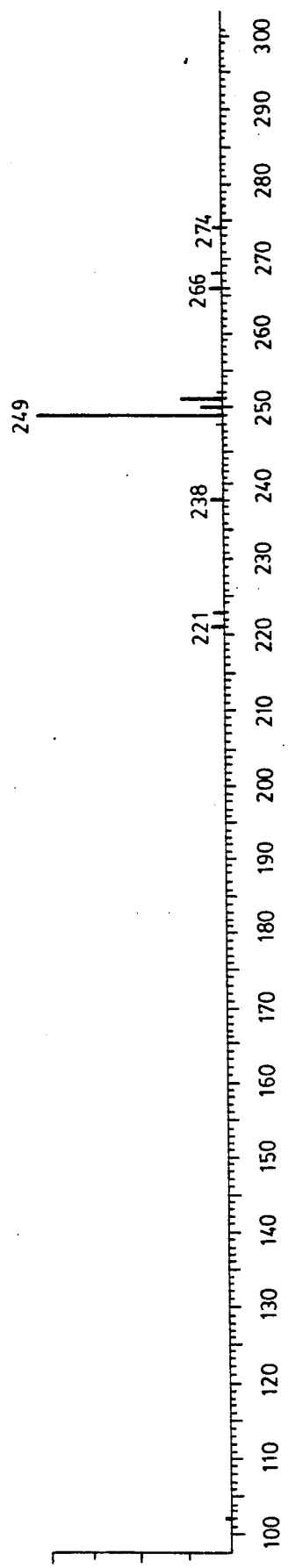
FIG. 1—Mass spectrum of 7-chloro-4-hydroxy-2-quinoline carbonyl azide

A preferred embodiment of the invention comprises a 7-chloro-4-hydroxy-2-quinoline carbonyl azide useful as a photoaffinity probe for labeling glycine binding sites of cell surface receptors, e.g., the glycine binding site of the NMDA receptor, and the glycine receptor of the spinal cord. Also included within the scope of the invention are other 4-hydroxyquinaldic acid derivatives suitable for use in labeling or pharmacologic modulation of the receptor site.

An additional aspect of the invention relates to a method for labeling the NMDA receptor complex with the compounds of the present invention. With this method, one first obtains a preparation containing the receptor. While this preparation can comprise any of a number of materials, preferably it will include a preparation of cortical membranes isolated as described in Example II. Of course, preparations derived from other suitable sources such as hippocampus, striatum, spinal cord or other nervous system regions can also be used. The preparation is exposed to a compound of the present invention, most preferably 7-chloro-4-hydroxy-2-quinoline carbonyl azide, under such conditions that the compound binds to the NMDA receptor, and the bound compound is irradiated with a light. As a result of this procedure, the bound compound undergoes a photochemical reaction forming a highly reactive nitrene and giving off a molecule of nitrogen gas. This nitrene intermediate has six valence electrons, and can exist in either of two energetically proximate states: a single zwitterion state or a triplet diradical state. Thus, it can readily undertake both nucleophilic and electrophilic attacks. The subsequent reaction of the nitrene with functional groups on the receptor macromolecule generates the covalent bond required for irreversible labeling.

The resultant labeled receptor complexes can be used to facilitate purification and characterization of the component proteins. For example, the present inventors have purified and characterized the receptor complex by electrophoresis through a polyacrylamide gel matrix. Because the labeled receptor molecules are fluorescent, they can be readily detectable in a gel. Alternatively, the labeled receptor may be identified through the use of compound which has been radiolabeled. In this case, detection would be by standard autoradiography and radioactive counting techniques. Radiolabeled compound is obtained by the normal synthetic pathway with the exception that the respective precursor is radiolabeled.

These and other aspects of the invention will become more readily apparent from the following examples. Although the examples serve to illustrate certain aspects of the invention, they are not intended to limit it unless specified in the claims.

EXAMPLE I

The following example describes synthesis of the 7-chloro-4-hydroxy-2-quinoline carbonyl azide, useful as a photoaffinity probe for labeling of the NMDA receptor complex. The example also describes synthesis of other 4-hydroxyquinaldic acid derivatives.

A. Synthesis of 7-Chloro-4-hydroxy-2-quinoline carbonyl azide

Unless otherwise noted, all procedures involving the azide were conducted under a photographic safe light. A mixture of diphenylphosphoryl azide (3.32 g, 12 mmol) in 5 mL N,N-dimethylformamide (DMF) was added dropwise to a mixture of 7-chloro-4-hydroxyquinaldic acid (2.7 g, 12 mmol) and triethylamine (1.5 g, 15 mmol) in 15 mL DMF. The resultant mixture was stirred for twelve hours. The mixture was then poured over ice and adjusted to a pH of 8.2 with sodium bicarbonate, and the product was collected by filtration and washed with acetone. A yield of 3.0 g (12 mmol) was obtained. Thin layer chromatography (TLC) (31% ethanol:38% n-butanol:23% chloroform: 8% ammonium hydroxide) gave one spot which was fluorescent under UV light ($R_f$=0.76. Infrared spectrometry (Nujol) showed the azide peak at 2160 cm$^{-1}$ In ethanol, the azide gave UV max at 355 and 252 nm. In 50 mM Tris acetate, an emission maximum was seen at 429.5 nm on excitation at 375 nm. Direct chemical ionization mass spectrometry with ammonia as reagent gas gave m/z 249, 251 (M+H)+. (FIG. 1)

B. Preparation of Other Comoounds

In addition to 7-chloro-4-hydroxy-2-quinoline carbonyl azide acid, which is preferred, the invention also encompasses a number of other compounds, including 7-bromo-4-hydroxy-2-quinoline carbonyl azide, 7-fluoro-4-hydroxy-2-quinoline carbonyl azide, 7-iodo-4-hydroxy-2-quinoline carbonyl azide, 6-methoxy-4-hydroxy-2-quinoline carbonyl azide, 7-chloro-6-methoxy-4-hydroxy-2-quinoline carbonyl azide and 5-chloro-4-hydroxy-2-quinoline carbonyl azide.

Production of these compounds may be accomplished by the following procedure.

A compound is selected from the following group: 7-bromo-4-hydroxyquinaldic acid; 7-iodo-4-hydroxyquinaldic acid; 7-fluor-4-hydroxy quinaldic acid; 6-methoxy-4-hydroxyquinaldic acid; 7-chloro-6-methoxy-4-hydroxyquinaldic acid; and 5-chloro-4-hydroxyquinaldic acid. The compound selected is then reacted with the diethyl ester of oxaloacetic acid (prepared b reacting the acyl chloride with ethyl alcohol). The product is then heated in mineral oil at 250° C. to produce the corresponding quinoline derivative. Isomers are separated by recrystallization from pyridine and/or acetic acid. Basic hydrolysis of the ester produces the substituted 4-hydroxyquinaldic acid (Surrey and Hammer, *J. Amer. Chem. Soc.*, 68:113-116 (1946)), which is then used to produce the substituted azide, amide, or isocyanate.

The azides are produced following the procedure set forth in Example I.

If desired, the azide compounds may be converted to the corresponding isocyanate by decomposition under anhydrous conditions. This may be achieved, for example, by refluxing in benzene or toluene.

Amide derivatives may be synthesized by the following procedure.

Substituted 4-hydroxyquinaldic acid compounds are prepared and reacted with thionyl chloride to produce the corresponding acid chloride. Corresponding amides can then be produced by reacting the acid chloride with ammonium acetate, or by reacting a substituted amine o amine salt with the acid chloride in the presence of potassium carbonate.

The azides and isocyanates may be used as labels. The amide derivatives may be used for pharmacologic modulation of the nervous system glycine binding sites.

EXAMPLE II

The following example describes the use of the 7-chloro-4-hydroxy-2-quinoline carbonyl azide in labeling of the NMDA receptor.

A. Preparation of Cortical Membrane Containing NMDA Receptors $^3$H-Glycine ($^3$H-GLY), $^3$H-TCP and NMDA specific $^3$H-GLU binding assays were performed in a buffy coat rat cortical membrane preparation (Jones et al., 1989). The tissue was homogenized in a glass grinding vessel with a teflon pestle in ice-cold 0.32M sucrose and centrifuged for 10 min at 1000× g. The resultant supernatant was decanted and recentrifuged at 20,000× g for 20 min. The pellet was resuspended in 20 volumes of ice-cold dH$_2$O and centrifuged for 20 min at 8000× g. The supernatant and the buffy coat were then re-collected and recentrifuged at 48,000× g for 20 min. The pellet was resuspended in 20 volumes of icecold water and centrifuged for 20 min at 48,000× g, after which it was stored at −20° C. for not more than two weeks. On the day of the assay, the pellet was thawed, resuspended in 40 volumes of buffer, incubated at 37° C. for 20 min in the appropriate buffer, and centrifuged for 10 min at 48,000× g. The pellet was then resuspended in 40 volumes of buffer and recentrifuged at 48,000× g for 10 min. This step was repeated twice before the pellet was finally resuspended in a buffer suitable for the particular binding assay. Protein concentrations were determined by the method described by Smith (1985).

B. NMDA-specific $^3$H-Glutamate Binding Assay $^3$H-glutamate binding assays were initiated by adding 100 µl aliquots of membrane homogenate (100–150 µg protein) to test tubes containing 10 nM $^3$H-L-glutamate in the presence or absence of the test drug(s) dissolved in 50 nM Tris acetate buffer pH 7.4 for a final volume of 1 ml. Tubes were incubated for 30 min at 4° C.

For equilibrium saturation experiments, different concentrations of $^3$H-glutamate (diluted with unlabeled L-glutamate) ranging from 10 to 320 nM in the presence or absence of test drug(s) were examined Non-specific binding was defined as that remaining in the presence of 300 µM NMDA and was etermined at the lowest and the highest concentration of $^3$H-L-glutamate. Non-specific binding at intermediate concentrations was estimated by interpolation between these two points The samples were filtered over GF/C filters on a Brandel M-24 cell harvester followed by washing with 10 ml ice cold buffer over a six second period The filters were placed into scintillation vials and five ml Safety-solve scintillation cocktail (Research Products International Corp, Mount Prospect, Ill.) were added. All vials were vortexed and allowed to sit a minimum of two hours before counting Liquid scintillation spectroscopy was performed using a Beckman LS5000 TD counter with a counting efficiency of 39%.

$^3$H-Glycine Binding Assay $^3$H-glycine binding assays were initiated by addition of 100 µl aliquots of membrane homogenate (100–150 µg protein) to test tubes containing 20 nM $^3$H-glycine in the presence or absence of the test drug(s) dissolved in 50 mM Tris acetate or 50 mM Na-free free HEPES buffer pH 7.5 for a final volume of 1 ml, followed by incubation for 30 min at 4° C. For equilibrium saturation experiments, concentrations of $^3$H-glycine (diluted with unlabeled glycine) ranging from 20 to 1,280 nM in the presence or absence of test drug(s) were examined. Non-specific binding was defined as that remaining in the presence of 1 mM glycine. The filtration procedure and scintillation counting were performed as described above.

$^3$H-TCP Binding Assay

The dissociative anesthetics ketamine and phencyclidine (PCP) selectively antagonize depolarizations produced by NMDA. This action is a result of drug binding within the ion channel of the activated NMDA receptor channel complex. Glycine will produce an increase in this binding due to its allosteric effect on receptor activation. However, a glycine receptor antagonist (a compound which binds but does not activate the receptor) will cause a decrease in PCP binding due to the resultant decrease in channel opening. TCP (the thienyl derivative of PCP) is used to assay for this glycine effect on channel activation.

$^3$H-TCP binding assays were initiated by addition of 100 μl aliquots of membrane homogenate (approximately 150 μg protein) to test tubes containing 5 nM $^3$H-TCP in the presence or absence of the test drug(s) dissolved in 10 mM HEPES buffer pH 7.5. The final volume in each tube was 1 ml, and tubes were incubated for 2 hr at 23° C. Non-specific binding was defined as that remaining in the presence of 30 μM PCP. The filtration procedure was used as described above except that the filters were presoaked for one hour in 0.03% polyethyleneimine (PEI) (Sigma) to reduce filter binding. Scintillation counting was performed as described above.

E. Photolabeling with 7-chloro-4-hydroxy-2-quinoline carbonyl azide

The 7-chloro-4-hydroxy-2-quinoline carbonyl azide had limited solubility in polar solutions. Thus, in all experiments, 7-chloro-4-hydroxy-2-quinoline carbonyl azide was first dissolved at high concentrations (1–10 mM) in dimethylsulfoxide (DMSO) and then diluted in the appropriate physiological buffer. The final DMSO concentration in various experiments varied between 0.1 and 5%, with higher DMSO concentrations required to maintain solubility of 7-chloro-4-hydroxy-2-quinoline carbonyl azide at higher concentrations. The appropriate DMSO control was performed at the same time, and no changes in the binding of radioligands were ever observed. This procedure, and all subsequent procedures where non-photolyzed material was desired, were performed under red light.

Preliminary experiments demonstrated that optimum photolysis occurred under the following conditions. Previously washed rat cortical membranes were resuspended at approximately 0.1 mg protein/ml in the appropriate buffer (pH 7.4 at 23° C.), and 30 ml were placed in each of 3 or 4 150×25 mm polystyrene culture dishes on a rotating shaker. A 200 μL aliquot of a 10 mM solution of 7-chloro-4-hydroxy-2-quinoline carbonyl azide dissolved in DMSO was added and the solution was mixed for 10 min in the dark. Photolysis was accomplished by exposure of the reaction mixture to 366 nm long-wave ultraviolet light (Transilluminator, Fotodyne, Model 3-3000) at a distance of 5 cm for 10 min with continuous mixing.

F. Computer Analysis of Binding Data

The Hill slopes (nH) and maximal displacement of radioligand binding were estimated by non-linear curve-fitting to a sigmoidal algorithm using the EBDA portion of the LIGAND data analysis software package for the IBM-PC (Elsevier). $K_1$ values were obtained from the LIGAND analysis of the same data. $K_D$ and $B_{max}$ estimates were obtained by non-linear curve-fitting of the saturation isotherm using programs from the same software package (Munson and Rodbard, 1980). All data analysis was performed on each of 3–7 individual experiments performed in triplicate (7 concentrations) or duplicate (10 concentrations). Reported values are the mean ±S.E.M. of these analyses. For displacement experiments, these values were plotted with the sigmoid curve taken as the average of the sigmoidal fits of each individual experiment.

G. Results of Binding Studies

Figure 2A:
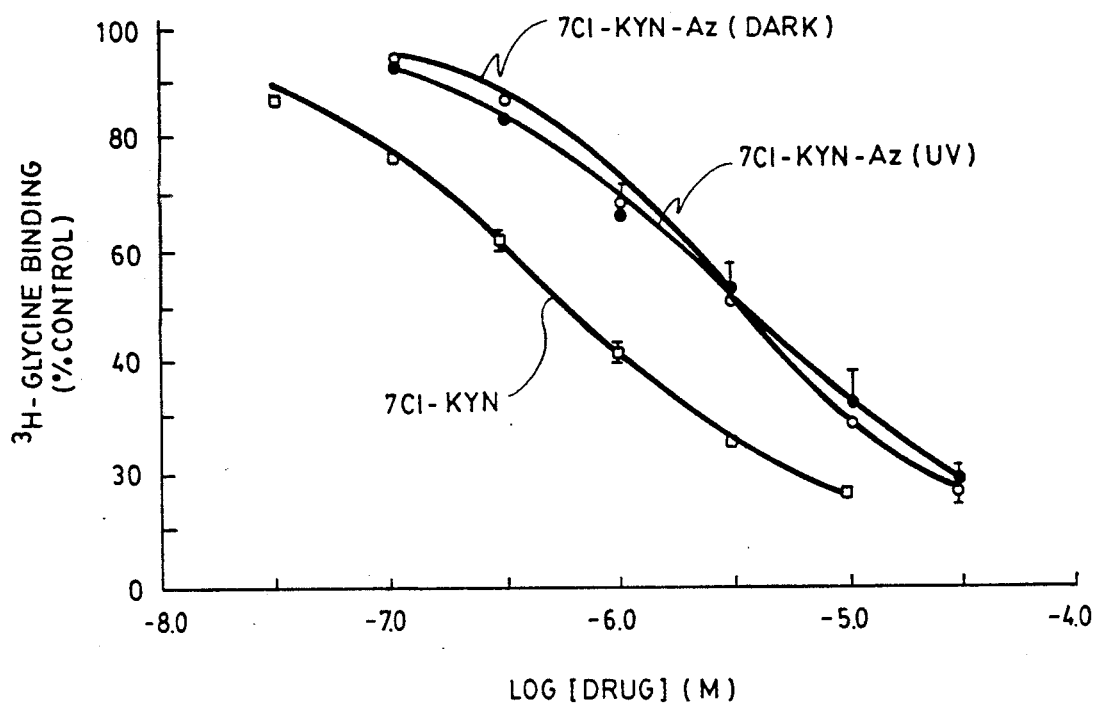
FIG. 2—Inhibition of Glycine (a) or Glutamate (b) binding to NMDA receptors. (Abbreviations: 7Cl-KYN for 7-chloro-4-hydroxyquinaldic acid; 7Cl-KYN-Az for 7-chloro-4-hydroxy-2-quinoline carbonyl azide)

Initial experiments were designed to determine the relative affinity of 7-chloro-4-hydroxy-2-quinoline carbonyl azide for the NMDA recognition site vs. the strychnine-insensitive glycine site associated with the NMDA receptor/channel complex. In experiments conducted under a photographic safe ("red") light to prevent incidental photolysis, 7-chloro-4-hydroxy-2-quinoline carbonyl azide was able to displace $^3$H-glycine binding from rat cortical membranes with relatively high affinity ($K_1$=2.4±0.2 μM; n=3) in an apparently competitive fashion (nH=0.90±0.08; FIG. 2A). In parallel experiments, 7-chloro-4-hyroxyquinaldic acid displaced $^3$H-glycine binding with a $K_i$ value of 0.49±0.05 μM and a Hill slope of 0.74±0.03 (n=4). The introduction of an azido group resulted in a 5-fold decrease in the apparent affinity for the $^3$H-glycine binding site. The affinity compares favorably, however, with that reported for another competitive antagonist at the glycine site HA-966 ($K_1$~5 μM) that has been shown to reduce NMDA-mediated neuronal response in a glycinereversible manner (Fletcher and Lodge, 1988).

Figure 2B:
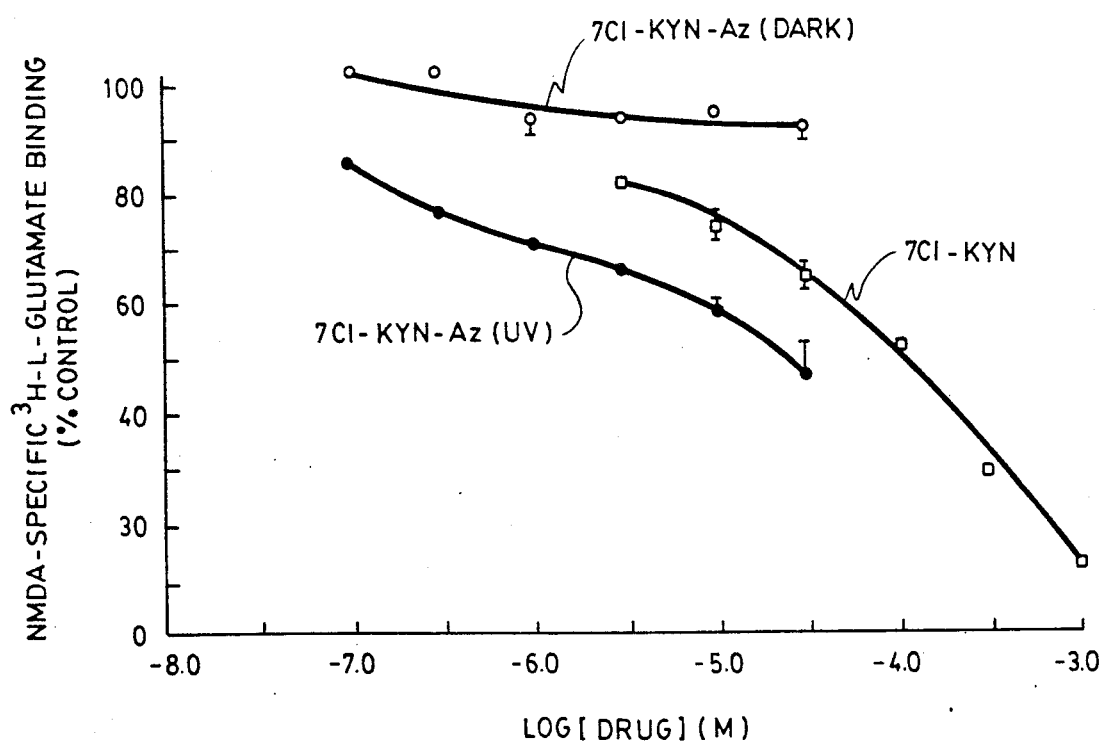
Figure 3:
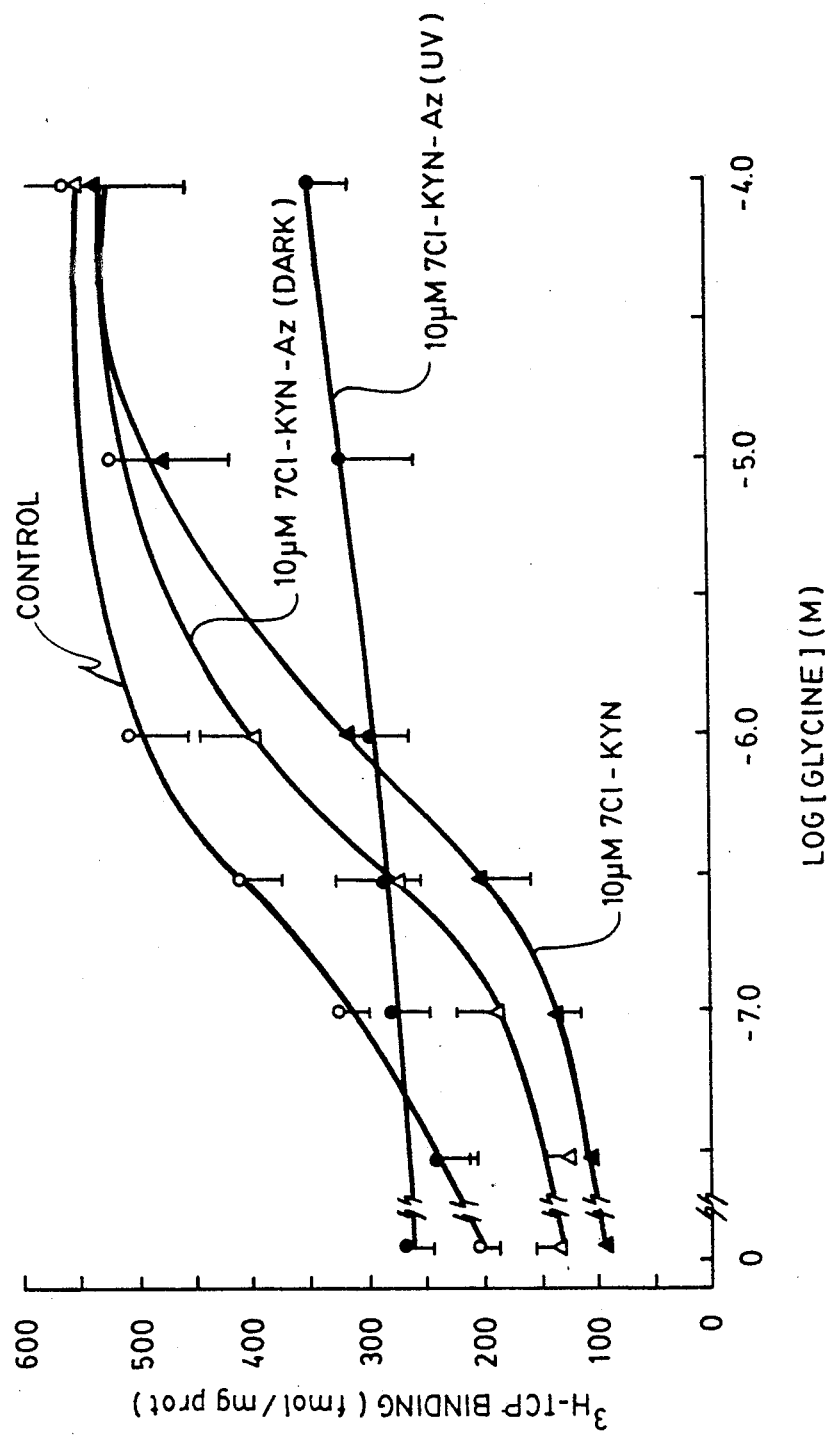
FIG. 3—Glycine enhanced $^3H$TCP bind in cortical membranes. (Abbreviations: 7Cl-KYN for 7-chloro-4-hydroxyquinaldic acid; 7Cl-KYN-Az for 7-chloro-4-hydroxy-2quinoline carbonyl azide)
Figure 4:
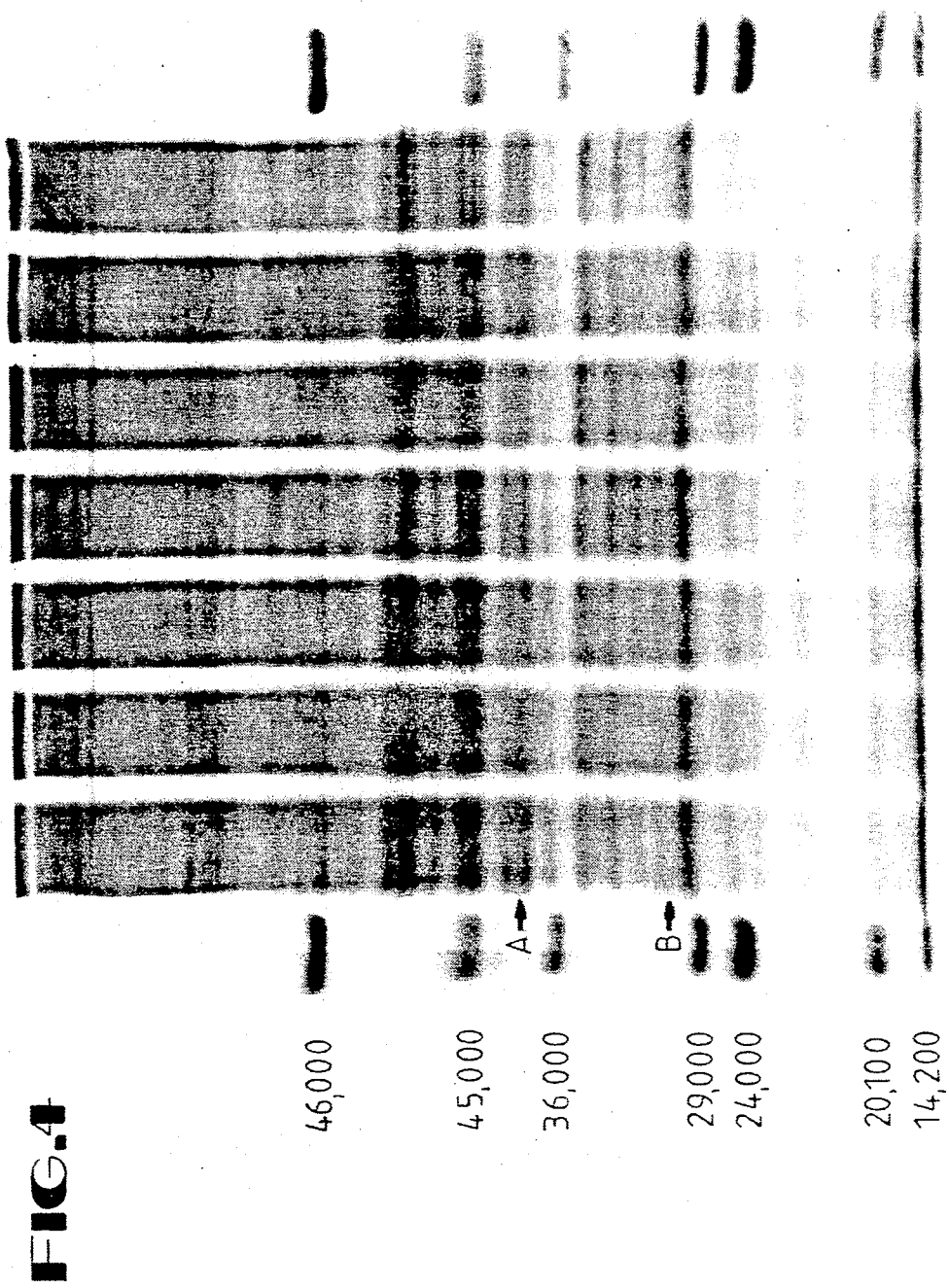
FIG. 4—Polyacrylamide SDS Gel of Cortical Membrane Proteins. Gel was stained with Coomassie Blue.
Figure 5:
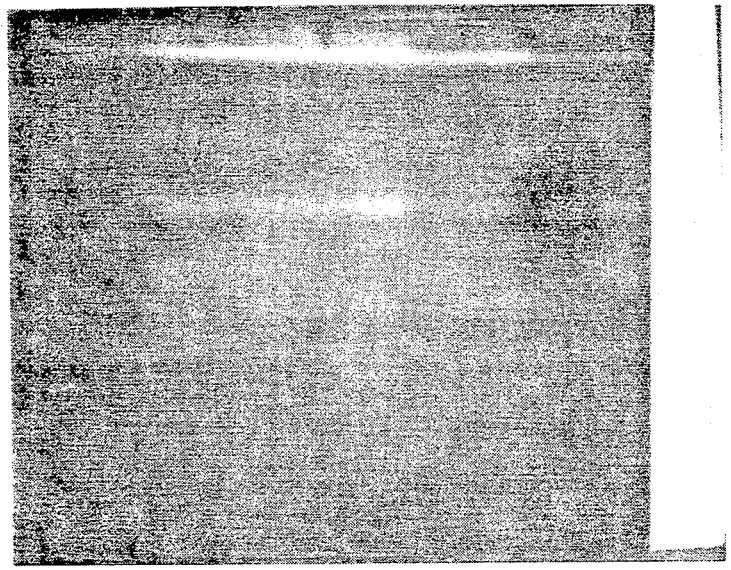
FIG. 5—Polyacrylamide Gel depicted in FIG. 4, viewed with UV light. Fluorescent bands depict labeled NMDA receptor proteins.

As shown in FIG. 2B, 7-chloro-4-hydroxy-2-quinoline carbonyl azide displaced less than 10% of NMDA-specific $^3$H-L-glutamate binding from rat cortical membranes. Thus, the introduction of an azido group lowers the affinity for the NMDA site ($K_1$=101±12 μM; nH=0.86±0.05; n=5) and makes the compound more selective for the glycine site. Therefore, under chloro-4-hydroxy-2-quinoline carbonyl azide, few if any NMDA recognition sites would be expected to be labeled.

In other studies, glycine enhanced $^3$H-TCP binding in cortical membranes was measured. The concentration-dependent increase in $^3$H-TCP binding produced by glycine is due to an allosteric increase in the frequency of channel opening produced by NMDA receptor activation (Johnson and Asoher, 1987). In cortical membranes exposed to 10 min of UV irradiation without added 7-chloro-4-hydroxy-2-quinoline carbonyl azide, glycine increased $^3$H-TCP binding with an $EC_{50}$ of 192 nM (95% C.L. 90–408 nM; slope=1.02) and a maximal 150% at 1–100 μM. The potency of glycine in this assay is in excellent agreement with the affinity of glycine for the strychnine-insensitive $^3$H-glycine site associated with the NMDA receptor/channel complex (~200 nM). In tissue treated with the reversible glycine antagonist, 7-chloro-4-hydroxyquinaldic acid and exposed to UV light, $^3$H-TCP binding in the absence of added glycine was reduced by 100%, and the glycine concentration-response curve was shifted 4-fold to the right in a parallel fashion ($EC_{50}$=928 nM; 95% C.L. 334–2575 nM; slope=0.93). When the membranes were treated with 10 μM 7-chloro-4-hydroxy-2-quinoline carbonyl azide but not exposed to UV light, the decrease in the absence of added glycine was somewhat smaller (70%) and the shift in the glycine concentration response curve was not as pronounced ($EC_{50}$=469 nM; 95% C.L. 209–1053 nM; slope=1.15). When the membranes were UV irradiated in the presence of 10 μM 7-chloro-4-hydroxy-2-quinoline carbonyl azide, the maximal enhancement of $^3$H-TCP binding by glycine was greatly reduced (30%). This was accompanied by a small (35%)

but consistent increase in ³H-TCP binding in the absence of added glycine.

The actions of the non-photolyzed 7-chloro-4-hydroxy-2-quinoline carbonyl azide are entirely consistent with a competitive antagonism of the actions of glycine. The decrease in ³H-TCP binding in the absence of added glycine is most likely due to inhibition of endogenous glycine remaining in the membranes after washing. In contrast, UV irradiation of tissue incubated in the presence of 7-chloro-4-hydroxy-2-quinoline carbonyl azide produced a distinctly non-competitive inhibition of glycine-enhanced ³H-TCP binding. The small increase in ³H-TCP binding observed in these membranes is somewhat anomalous but may reflect partial agonist properties of the products that are formed in solution during UV irradiation or possibly a change in the receptor conformation when 7-chloro-4-hydroxy-2-quinoline carbonyl azide binds covalently to the glycine site.

In summary, the above experiments demonstrate that (1) 7-chloro-4-hydroxy-2-quinoline carbonyl azide has a selective affinity for the ³H-glycine binding site relative to the NMDA recognition site labeled by ³H-L-glutamate (2) this compound can competitively antagonize the enhancement of ³H-TCP binding by glycine at this site, and (3) UV irradiation of cortical membranes in the presence of this compound produced a large non-competitive loss of glycine-enhanced ³H-TCP binding that is consistent with an irreversible blockade of the glycine binding site.

III. POLYACRYLAMIDE GEL ELECTROPHORESIS OF THE NMDA ASSOCIATED GLYCINE RECEPTOR

The following example describes use of the 7-chloro-4-hydroxy-2-quinoline carbonyl azide to label NMDA receptors for characterization and purification.

A. Gel Electrophoresis

Polyacrylamide slab gel electrophoresis (10% acrylamide in 2.7% NaDodSO$_4$) was used to resolve membrane proteins. The electrode buffer (pH 8.3) contained 0.025 M Tris, 0.192 M glycine, and 0.1% NaDodSO$_4$, and the gels were stained with Coomassie blue. The gels were placed over an ultraviolet source for visualization of fluorescent bands. Bovine serum albumin (66,000 M$_r$), ovalbumin (45,000 M$_r$), glyceraldehyde-3-phosphate dehydrogenase (36,000 M$_r$), carbonic anhydrase (29,000 M$_r$), trypsinogen (24,000 M$_r$), trypsin inhibitor (20,000 M$_r$) and α-lactalbumin (14,200 M$_r$) were used as molecular weight markers.

Cortical membranes were photolabeled with 7-chloro-4-hydroxy-2-quinoline as described in Example II, section E. Protein concentration of this preparation was determined using the BCA protein assay kit (Pierce, Rockford, Ill.). This allowed the loading of a known amount of protein on each lane of the gel.

Labeled membrane samples were then diluted 1:1 with 2× treatment buffer (0.125 M Tris-Cl, pH 6.8, 4% SDS, 20% glycerol, 10% 2-mercaptoethanol, 0.01% bromophenol blue) and boiled for 90 seconds. Samples were cooled and loaded onto gels using a Hamilton Syringe. Volumes were manipulated to give protein concentrations of 100 ug/well for each sample and 50 uq/well for molecular weight standards.

Discontinuous SDS-polyacrylamide gels (10% acrylamide-2.7% methylenebisacrylamide) were run as described by Laemmli (1970) 10 with Tris-glycine-SDS tank buffer (0.025 M Tris, pH 8.3, 0.192M glycine, 0.1% SDS). Vertical slab gels (180×160×1.5mm; Hoefer Scientific Instruments, San Francisco, Calif.) were electrophoresed at 30 ma/gel (ISCO Model 494 power supply, ISCO, Lincoln, NE) for 5-6 hours until the tracking dye (bromophenol blue) migrated within 1 cm of the bottom edge of the gel.

Gels were removed and fluorescent bands visualized and recorded using a transilluminator (Fotodyne, New Berlin, Wis.) fitted with four 366nm UV bulbs (15 watts). Gels were stained with Coomassie brilliant blue (0.125% Coomassie blue R-250, 50/5 methanol, 10% acetic acid) with gentle shaking for 4-8 hours. Gels were destained by diffusion, first using 50% methanol-10% acetic acid for 1 hour, then 7% acetic acid-55% methanol overnight or until background cleared. Molecular weights of the migrated fluorescent bands were derived from stained simultaneously run molecular weight standards.

Significantly, the SDS polyacrylamide gel electrophoresis yielded two distinct fluorescent bands, indicating that protein localized in those bands constituted a substantially purified preparation of an NMDA receptor protein. The broadest and brightest band migrated the furthest ($R_f=0.71$) and had a calculated molecular weight of 28,700 Daltons. The molecular weight of the smaller band ($R_f=0.53$) was calculated to be 42,950.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

It is apparent that the invention may also be utilized, with suitable modifications within the state of the art. It is the Applicants intention in the following claims to cover all such equivalent modifications and variations which fall within the true spirit ,and scope of the invention.

REFERENCES

The following references which were listed in the above referenced disclosure are incorporated herein by reference. Inclusion of a reference in this list is not intended to and does not constitute an admission that such reference represents prior art with respect to the present invention.

1. Fletcher, E. J. and D. Lodge; "Glycine reverses antagonism of N-methyl-D-aspartate by 1-hydroxy-3-aminopyrrolidone-2 (HA-66) but not by D-2-amino-5-phosphonovalerate (D-AP5) on rat cortical slices"; *Journal of Pharmacology* 151:161-162, 1988.

2. Johnson, J. W. and P. Ascher; "Glycine potentiates the NMDA response in cultured mouse brain neurons"; *Nature* 325: 549-531, 1987.

3. Jones, S. M., L. D. Snell and K. M. Johnson; "Characterization of the binding of radioligands to the N-methyl-D-aspartate, phyncyclidine, and glycine receptors in buffy coat membranes"; *Journal of Pharmacological Methods* 21:161-168, 1989.

4. Kemp, J. A., A. C. Foster, P. D. Leeson, T. Priestly, R. Tridgett, L. L. Iversen and G. N. Woodruff; "7-Chlorokynurenic acid is a selective antagonist of the glycine modulatory site of the N-methyl-D-aspartate receptor complex"; *Proceeds of the National Academy of Science USA* 85:6547-6550, 1988.

5. Laemmli, U. K.; "Cleavage of Structural Proteins During the Assembly of the Head of Bacteriophage T4"; *Nature* 227:680, 1970.

6. Munson, P. J. and D. Rodbard; "LIGAND: A versatile computerized approach for the characterization of ligand binding systems"; *Analytical Biochemistry* 107:220-239, 1980.

7. Smith, P. K., R. I. Krohn, G. T. Hermanson, A. K. Mallia, F. H. Gartner, M. D. Provenzano, E. K. Fujimoto, N. M. Goeke, B. J. Oson and D. C. Klenk; "Measurement of protein using bicinchininic acid"; *Analytical Biochemistry* 150:76-85, 1985.

8. Surrex, Alexander and H. F. Hammer; "Some 7-substituted 4-aminoquinoline derivatives"; *Journal of the American Chemical Society* 68:113-116, 1946.

What is claimed is:

1. A compound having the formula:

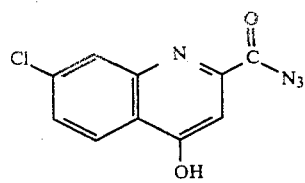

2. A compound having the formula:

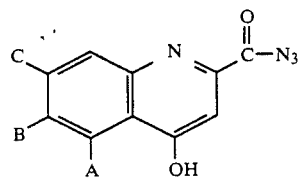

wherein A is chloro or hydrogen; wherein B is methoxy or hydrogen; and wherein C is chloro, bromo, iodo, or fluoro.

3. A compound having the formula:

wherein A is azide;
wherein B is chloro or hydrogen;
wherein C is methody or hydrogen; and
wherein D is chloro, bromo, iodo, fluoro, or hydrogen.

4. A compound having the formula:

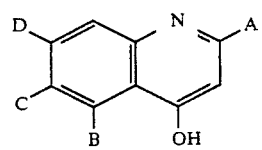

wherein A is isocyanate;
wherein B is chloro or hydrogen;
wherein C i methoxy or hydrogen; and
wherein D is chloro, bromo, iodo, fluoro, or hydrogen.

5. A compound having the formula:

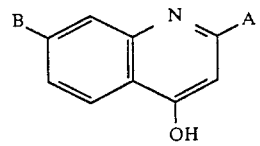

wherein A is azide; and
wherein B is chloro, bromo, iodo, or fluoro.

6. A compound having the formula:

wherein A is isocyanate; and
wherein B is chloro, bromo, iodo, or fluoro.

7. A compound having the formula:

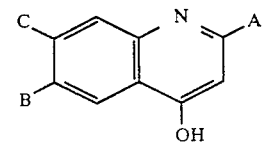

wherein A is azide;
wherein B is methoxy; and
wherein C is chloro or hydrogen.

8. A compound having the formula:

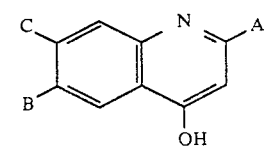

wherein A is isocyanate;
wherein B is methoxy; and
wherein C is chloro or hydrogen.

9. A compound having the formula:

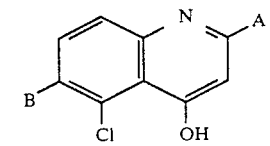

wherein A is azide; and
wherein B is methoxy or hydrogen.

10. A compound having the formula:

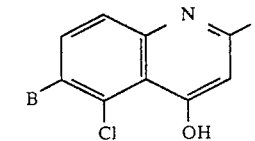

wherein A is isocyanate; and
wherein B is methoxy or hydrogen.

11. A compound having the formula:

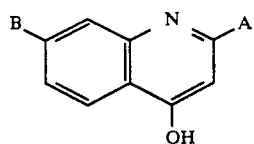

wherein A is azide; and
wherein B is a halogen or hydrogen.

12. A compound having the formula:

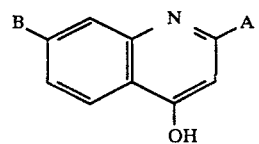

wherein A is isocyanate; and
wherein B is halogen or hydrogen.

13. A compound having the formula:

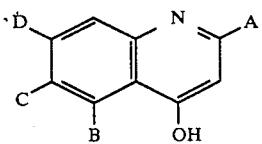

wherein A is azido carbonyl;
wherein B is chloro or hydrogen;
wherein C is methoxy or hydrogen; and
wherein D is chloro, bromo, iodo, fluoro, or hydrogen.

14. A compound having the formula:

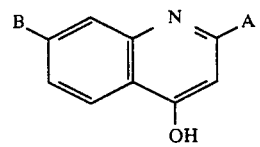

wherein A is azido carbonyl; and
wherein B is chloro, bromo, iodo, or fluoro.

15. A compound having the formula:

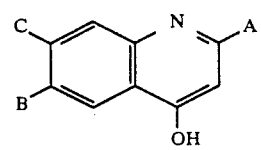

wherein A is azido carbonyl;
wherein B is methoxy; and
wherein C is chloro or hydrogen.

16. A compound having the formula

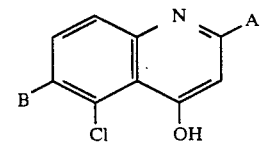

wherein A is azido carbonyl; and
wherein B is methoxy or hydrogen.

17. A compound having the formula:

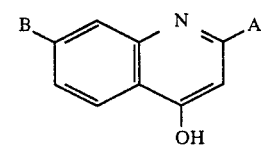

wherein A is azido carbonyl; and
wherein B is a halogen or hydrogen.

* * * * *

UNITED STATES PATENT AND TRADEMARK OFFICE
CERTIFICATE OF CORRECTION

PATENT NO. : 5,028,707
DATED : Jul. 2, 1991
INVENTOR(S) : Nichols et al.

It is certified that error appears in the above-identified patent and that said Letters Patent is hereby corrected as shown below:

In column 6, line 33, please replace "etermined" with --determined--.

In column 6, line 42, please replace "Ill." with --IL--.

In column 6, line 44, after "counting" please add a period.

In column 7, line 1, delete "15".

UNITED STATES PATENT AND TRADEMARK OFFICE
CERTIFICATE OF CORRECTION

PATENT NO. : 5,028,707
DATED : Jul. 2, 1991
INVENTOR(S) : Nichols et al.

It is certified that error appears in the above-identified patent and that said Letters Patent is hereby corrected as shown below:

In column 8, line 5, please replace "Bindino" with --Binding--.

In column 8, line 18, please replace "K;" with --$K_1$--.

In column 8, line 35, after the term "under" please add -- the conditions used for photolabeling the membranes with 7- --.

In column 9, line 60, replace "0.0i%" with --0.01%--.

UNITED STATES PATENT AND TRADEMARK OFFICE
CERTIFICATE OF CORRECTION

PATENT NO. : 5,028,707
DATED : Jul. 2, 1991
INVENTOR(S) : Nichols et al.

It is certified that error appears in the above-identified patent and that said Letters Patent is hereby corrected as shown below:

In column 9, line 68, delete "10".

In column 10, line 52, replace "HA-66" with --HA-966--.

Column 11, line 6, replace "Analvtical" with
   --Analytical--.

Column 11, line 51, replace "methody" with --methoxy--.

Column 11, line 65, replace "i" with --is--.

Signed and Sealed this

Twenty-ninth Day of December, 1992

*Attest:*

DOUGLAS B. COMER

*Attesting Officer*   Acting Commissioner of Patents and Trademarks